US00PP22503P3

(12) United States Plant Patent
Hwang

(10) Patent No.: US PP22,503 P3
(45) Date of Patent: Feb. 21, 2012

(54) BANANA PLANT NAMED 'SMT-6'

(50) Latin Name: *Musa accuminata cavendishii*
Varietal Denomination: SMT-6

(75) Inventor: Shin-Chuan Hwang, Pingtung (TW)

(73) Assignee: Sumifru Singapore, Pte. Ltd., Singapore (SG)

( * ) Notice: Subject to any disclaimer, the term of this patent is extended or adjusted under 35 U.S.C. 154(b) by 0 days.

(21) Appl. No.: 12/802,902

(22) Filed: Jun. 15, 2010

(65) Prior Publication Data

US 2011/0307982 P1 Dec. 15, 2011

(51) Int. Cl.
*A01H 5/00* (2006.01)

(52) U.S. Cl. ..... Plt./160

(58) Field of Classification Search ..... Plt./160
See application file for complete search history.

*Primary Examiner* — Susan McCormick Ewoldt

(74) *Attorney, Agent, or Firm* — Klarquist Sparkman, LLP

(57) ABSTRACT

The 'SMT-6' variety is distinguished from other banana varieties due to the following unique combination of characteristics: Erect (Upright) foliar arrangement, compact bunch appearance, shorter fingers, and bunch (rachis) position.

4 Drawing Sheets

Latin name of the genus and species of the plant claimed:
Latin Name: *Musa accuminata cavendishii.*
Variety denomination: 'SMT-6'.

BACKGROUND

The present invention relates to a new and distinct variety of banana plant named 'SMT-6'. The new plant (mutant) was found in a commercial farm growing with the variety 'Giant Cavendish' (unpatented). The seedlings used for planting on this farm were derived from tissue culture method, which followed the protocol published by Ma & Shii ("In vitro formation of adventitious buds in banana shoot apex following decapitation" 18:135-42, 1972) and by Hwang et al. (HortScience 19:231-33, 1984). The 120 samples of mutant plant were derived from In-vitro culture technique used in the farm observation. The resulting plant was selected when growing in a cultivated area in T'boli, Mindanao, Philippines.

SUMMARY

The 'SMT-6' variety is distinguished from other banana varieties due to the following unique combination of characteristics: Erect (Upright) foliar arrangement, compact bunch appearance, shorter fingers, and bunch (rachis) position. The new variety has erect leaves, shorter finger (16.76 cm), and one side petiode formation. The erect leaf habit, shorter finger length, asymmetrical petioles arrangement, compact bunch and position observed 'SMT-6' are not found among all known *Musa cavendishii* varieties. A comparison of the closest varieties 'Giant Cavendish' (unpatented), 'Granaine' (unpatented), 'Granaine' (unpatented) and 'Tall Williams' (unpatented) are shown in the table below):

| Feature | 'SMT-6' | 'Giant Cavendish' | 'Granaine' and 'Tall Williams' |
|---|---|---|---|
| Nodes | Very Compact | Wide nodes | Wide nodes |
| Leaf habit | Erect/upright | drooping | intermediate |

-continued

| Feature | 'SMT-6' | 'Giant Cavendish' | 'Granaine' and 'Tall Williams' |
|---|---|---|---|
| Petiole arrangement | asymmetrical | symmetrical | symmetrical |
| Finger length: $2^{nd}$ hand | 16.76 cm | 25.15 cm | 25.4 cm |
| Finger length: last hand | 11.43 cm | 18.29 cm | 17.78 cm |

The 'SMT-6' variety was developed as follows. The corm of the parent ('Giant Cavendish') was propagated and reproduced through tissue culture for seedling multiplication using the protocol published by Ma & Shii (1992) and Hwang et al. (1984). The tissue cultured seedlings of 'SMT-6' were then planted in T'boli, South Cotabato for further argonomic characterization and post-harvest evaluations. The corms of 'SMT-6' followers were further propagated and reproduced using the same tissue culture method of Ma & Shii and Hwang et al. The 'SMT-6' variety arose as a spontaneous whole plant mutation as was selected for its unique characteristics described above. 'SMT-6' has been asexually reproduced T'boli, Mindanao, Philippines, and after repeated propagation, the relevant characteristics of 'SMT-6' remain unchanged and sufficiently uniform. No evidence of off-types of 'SMT-6' has been observed or reported to us. Thus, it is concluded that 'SMT-6' is stable and reproduces true to type in successive generations of asexual reproduction.

The 'SMT-6' plants have been observed growing in a cultivated area in T'boli, Mindanao, Philippines. Certain characteristics of this variety, such as growth and color, may change with changing environmental conditions (such as, light, temperature, moisture, nutrient availability, or other factors). Color descriptions and other terminology are used in accordance with their ordinary dictionary descriptions, unless the context clearly indicates otherwise. Color designations are made with reference of the Munsell Color Chart.

Figure 1:
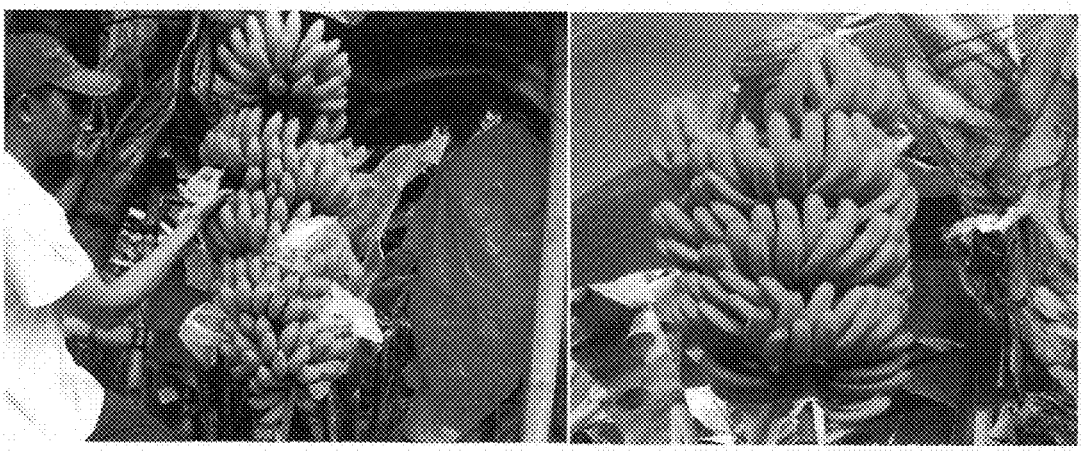
FIG. 1 are photographs showing fruit of the new variety 'SMT-6' as compared to the variety 'Giant Cavendish'.
Figure 2:
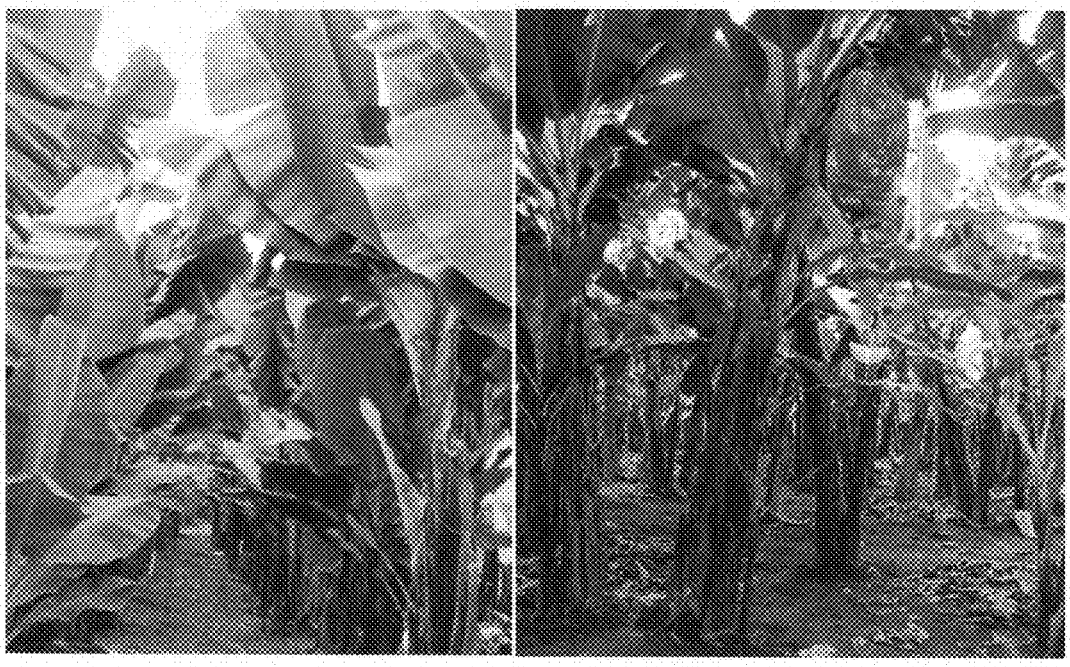
FIG. 2 are photographs showing leaves of the new variety 'SMT-6' as compared to the variety 'Giant Cavendish'.
Figure 3:
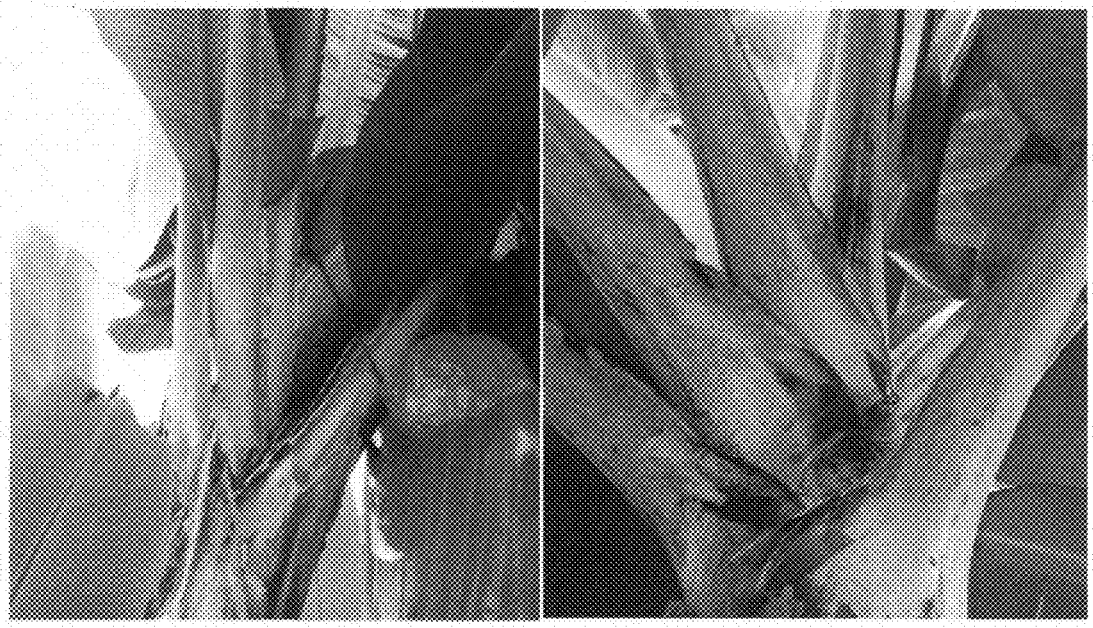
FIG. 3 are photographs showing the new variety 'SMT-6' as compared to the variety 'Giant Cavendish'.
Figure 4:
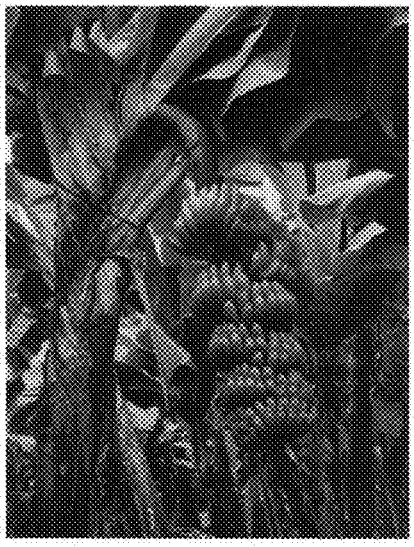
FIG. 4 are photographs showing the plant stand (foliage characteristics) of the new variety 'SMT-6' as compared to the variety 'Giant Cavendish'.
Figure 4:
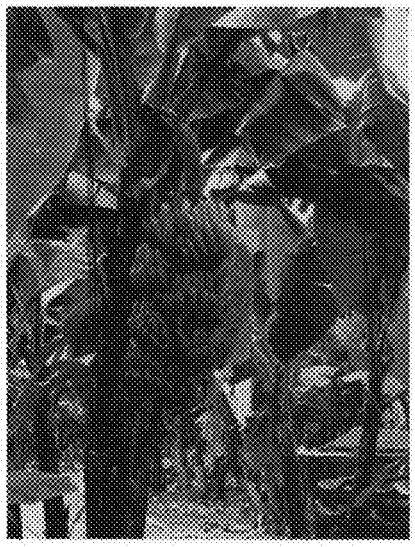
Figure 5:
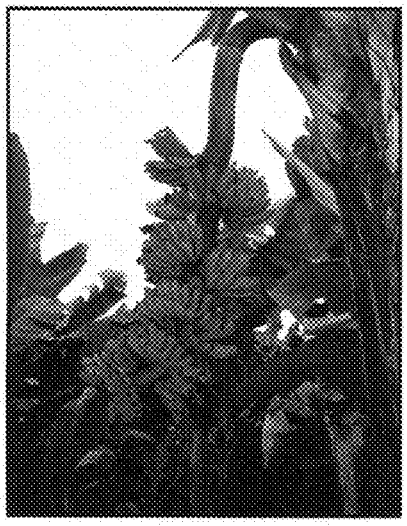
FIG. 5 are photographs showing the bunch position of the new variety 'SMT-6' as compared to the variety 'Giant Cavendish'.
Figure 5:
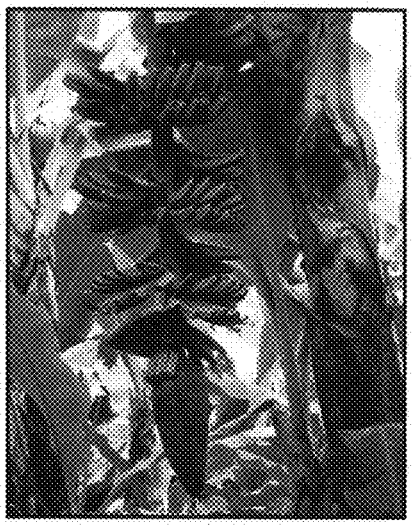
Figure 6:
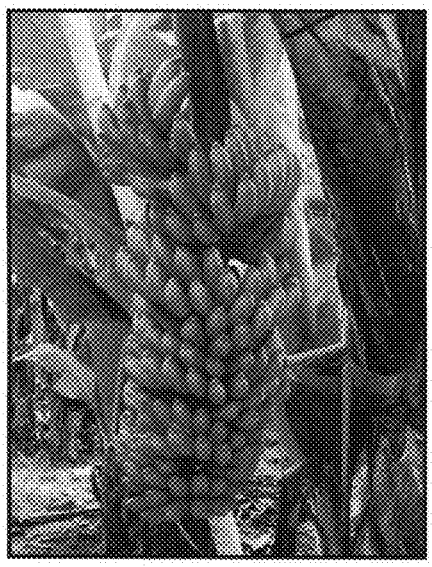
FIG. 6 are photographs showing the bunch appearance of the new variety 'SMT-6' as compared to the variety 'Giant Cavendish'.
Figure 6:
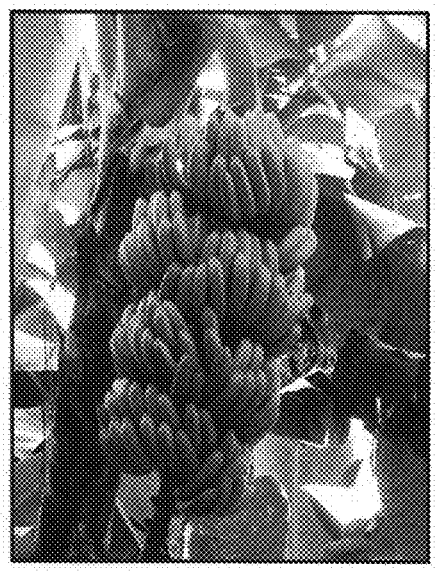
Figure 7:
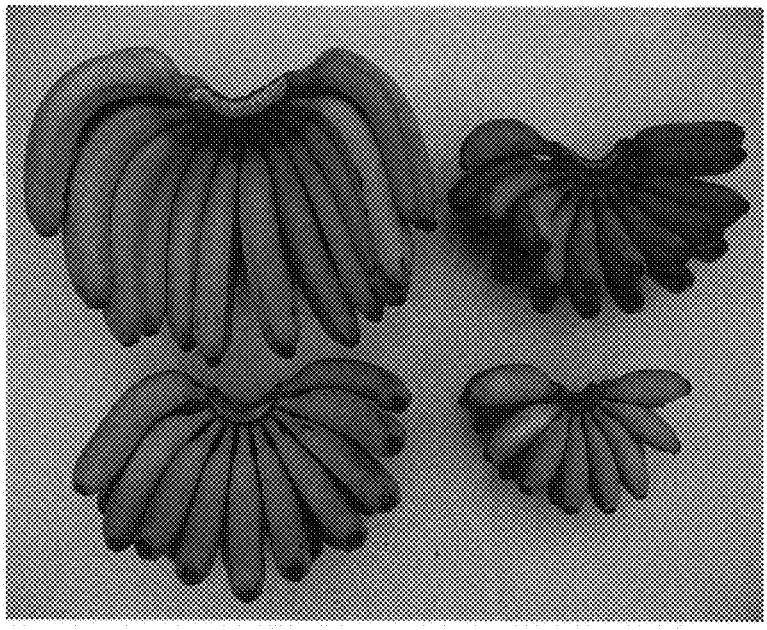
FIG. 7 are photographs showing the size of second and last hand fruit of the new variety 'SMT-6' as compared to the variety 'Giant Cavendish'.

The colors of an illustration of this type may vary with lighting and other conditions under which conditions and, therefore, color characteristics of this new variety should be determined with reference to the observations described herein, rather than from these illustrations alone.

BOTANICAL DESCRIPTION

The following detailed description of the 'SMT-6' variety is based on observations of 120 plants. The observed plants were 71 weeks of age and growing in T'boli, Mindanao, Philippines.

Latin name: *Musa acuminata 'Cavendishii'*

Use: Dessert fruit

Plant:

- *Vigor.*—Very vigorous 12.6% more than the regular Cavendish in terms of pseudostem girth size.
- *Overall shape.*—Erect/Upright leaf appearance.
- *Height.*—About 2.8 m — 3.05 m.
- *Width.*—Overall spread of about 2.2 m-2.6 m.
- *Sap.*—Watery-translucent in color.
- *Number of suckers.*—3.

Leaves: The length, width, thickness and other measurements were obtained from observations of three typical leaves in T'boli Mindanao, Philippines

- *Texture.*—Very corrugated, dull, & moderately waxy.
- *Sheen.*—Dull.
- *Length.*—About 2225 mm to about 2260 mm, averaging about 2242.5 mm.
- *Width.*—About 810 mm to about 900 mm, averaging about 855 mm.
- *Thickness.*—Similar to 'Giant Cavendish'.
- *Appearance of upper leaf surface.*—Dull.
- *Appearance of lower leaf surface.*—Dull.
- *Wax on leaves.*—Moderate.
- *Petiole.*—About <500 mm long and about 70-90 mm in diameter; Pink-purple to red (5R3/8 Munsell) in color.
- *Insertion point of leaf blades on petiole.*—Symmetric.
- *Shape of leaf blade base.*—One side rounded, one pointed.
- *Leaf corrugation.*—Very corrugated.
- *Margin.*—Crenate.
- *Tip shape.*—Obtuse blunt.
- *Form.*—Oblong.
- *Apex.*—Obtuse.
- *Base.*—One side rounded, one pointed.
- *Blotches on leaves of water sucker.*—Large purple blotches.
- *Venation.*—N/A.
- *Glands.*—N/A.
- *Stipules.*—N/A.
- *Leaf color.*—Upper leaf surface: Green 7.5GY3/2. Lower leaf surface: Medium Green 2.5GY5/2. Vein: Light Green 2.5GY 7/4. Color of midrib dorsal surface: Green/5GY 4/4. Color of midrib ventral surface: Light green/2.5GY 7/4. Color of cigar leaf dorsal surface: Green/5GY 5/6.
- *Pubescence.*—None.

Pseudostem:

- *Height.*—2.1 m to 2.9 m, 5.5 m in circumference.
- *Appearance.*—Shiny (not waxy).
- *Predominant underlying color.*—Pink-purple/10R 6/6.
- *Surface color.*—Medium Green 2.5GY6/8.
- *Pigmentation of the underlying pseudostem.*—Red/5R 3/10.
- *Wax on the leaf sheaths.*—Very little wax.
- *Development of sucker.*—Between ¼ & ¾ of the height of the parent plant.
- *Position of sucker.*—Close to parent (vertical growth).

Petiole/midrib/leaf:

- *Blotches at the petiole base.*—Large blotches.
- *Blotches color.*—Brown-black/5YR 3/2.
- *Petiole canal leaf III.*—Wide with erect margins.
- *Petiole margin.*—Not winged and clasping the pseudostem.
- Wing type.—Dry (based on International Network for the Improvement of Banana and Plantain descriptor) or shriveled.
- *Petiole margin color.*—Pink-purple to red/5R 3/8.
- *Edge of petiole margin.*—5R 3/8 in color.
- *Petiole margin width.*—>1 cm.

Bract:

- *Bract base shape.*—Small shoulder.
- *Bract apex shape.*—Pointed.
- *Bract imbrications.*—Old bract overlap at apex of bud.
- *Color of the bract.*—External face: Purple Brown/2.5YR ¾ internal face: Orange red/2.5YR 5/8 apex: Tinted with yellow (discolored). Color stripe on bract: Without discolored lines (not ridges) on the external face.
- *Bract scar on rachis.*—Very prominent.
- *Fading color on bract base.*—Color discontinuing towards the base (loss of pigmentation at the base).
- *Male bract shape.*—x/y>0.30 (ovate).
- *Male bract lifting.*—Lifting two or more at a time.
- *Bract behavior before falling.*—Revolute (rolling).
- *Wax on the bract.*—Moderately waxy.
- *Presence of grooves on the bract.*—Moderately grooving (parallel ridges are distinguishable).

Flowers:

- *Color.*—Unopened bud: Cream Opened flower: Cream.
- *Petal apex.*—Round.
- *Petal base.*—Folding.
- *Peduncle.*—310 mm — 600 mm in length, 70 mm — 120 mm width; Green/2.5GY 5/4; Slightly hairy; 1 empty node on peduncle.
- *Bunch position.*—Hanging at an angle of 45 degrees.
- *Bunch shape.*—Cylindrical-slightly truncated.
- *Bunch appearance.*—Very Compact.
- Flower that form the fruit.—Hermaphrodite (presence of pollen sacs and pollens).
- *Fruits.*—Biseriate and fused.

*Rachis type.*—Present and male bud may be degenerated or persistent.
*Rachis position.*—At an angle.
*Rachis appearance.*—Neutral/male flowers on the whole stalk without persistent bracts.
*Male bud type.*—Normal (present).
*Male bud shape.*—Intermediate.
*Male bud size.*—<20 cm in length.
*Anthers.*—Pink/Pink to Purple in color.
*Pistil.*—Red Purple in color.
*Pollen.*—Cream in color.
*Male flower behavior.*—Falling with the bract or falling after the bract.
*Compound tepal basic color.*—Cream.
*Compound tepal pigmentation.*—Rust-colored spots/10R 3/6.
*Lobe color of compound tepal.*—Yellow/5Y 8/10.
*Lobe development of compound tepal.*—Very developed.
*Free tepal colour.*—Translucent white.
*Free tepal shape.*—Rounded.
*Free tepal appearance.*—Several folding under apex (corrugated).
*Free tepal apex development.*—Little or no visible sign of development.
*Free tepal apex shape.*—Obtuse.
*Anther exertion.*—Inserted.
*Filament color.*—Cream.
*Style basic color.*—Red-purple/2.5R 6/8.
*Pigmentation on style.*—Cream.
*Style exertion.*—Inserted.
*Style shape.*—Curved twice.
*Stigma color.*—Yellow/2.5Y 8/8.
*Ovary shape.*—Arched.
*Ovary basic color.*—Cream.
*Ovary pigmentation.*—Very few or no visible sign of pigmentation.
*Dominant color of male flower.*—Yellow.
*Irregular flowers.*—1.

Fruit: Observed in T'boli, Minadanao, Philippines

*Fruit position.*—2$^{nd}$ Hand of bunch. Curved upward (obliquely, at a 45 degree angle upward).
*Number of fruits per hand.*—21 average (2$^{nd}$ hand).
*Size.*—About 16.76 cm long and 44.5 mm in diameter wide.
*Fruit shape (longitudinal curvature).*—Straight>slightly curved.
*Transverse section of fruit.*—Slightly ridges.
*Typical finger weight.*—127.96 g. (2$^{nd}$ hand).
*Form.*—Slight curvature.
*Fruit apex.*—Bottle-necked.
*Remains of flower relicts at fruit apex.*—Base of the style prominent.
*Fruit pedicel length.*—≧21 mm.
*Fruit pedicel width.*—5 mm — 10 mm.
*Pedicel surface.*—Hairless.
*Fusion of pedicels.*—No signs of fusion.
*Immature fruit peel.*—Light Green/5GY 6/8.
*Marture fruit peel.*—Yellow in color (does not match any color on the Munsell color chart).
*Fruit peel thickness.*—4 mm to 4.5 mm.
*Adherence of the fruit peel.*—Peel easily.
*Cracks in fruit peel.*—Depends on the fullness.
*Pulp in fruit.*—Pulp is present.
*Pulp color before maturity.*—White.
*Pulp color at maturity.*—Cream.
*Fruits fall from hands.*—Deciduous.
*Flesh texture.*—Smooth and firm.
*Predominant taste.*—Very sweet.
*Main use.*—Dessert.
*Presence of seed with source of pollen.*—N/A.
*Seed surface.*—N/A.
*Seed shape.*—N/A.
*Days from planting to first flowering.*—352.8.
*Number of leaves at flowering.*—13.
*Number of functional leaves (less than 15% of area necrotic) at flowering.*—13.
*Number of leaves at harvest.*—8.15 to 8.2.
*Number of functional leaves (less than 15% of area necrotic at harvest).*—8.15.
*Days from final bagging until harvest.*—72.1.
*Bunch weight.*—24 kg.
*Number of hands.*—12.4.
*Finger length.*—16.76 cm.
*Stalk weight.*—2.2 kg.
*Brix.*—23.1.
*Firmness.*—Pulp, 0.37; Core, 0.37.
*Number of fingers per bunch.*—256/18 finger/hand.
*Days from planting to shooting.*—50.4.
*Days from planting to harvest.*—62.2.
*Fruit production.*—First picking date at T'boli, Philippines in 2007 was about 9 bunches, and last picking date was On-going; average production is 24 kg of fruit per plant.
*Storage.*—Passed the Japan Market suitability test (Usually 5-6 days before discharge and maximum 4 days cold storage).

I claim:

1. A new and distinct variety of banana plant, substantially shown and described herein.

* * * * *

'SMT-6' 'GIANT CAVENDISH'

'SMT-6' 'GIANT CAVENDISH'

'SMT-6' 'GIANT CAVENDISH'

'SMT-6'

'GIANT CAVENDISH'

'SMT-6'

'GIANT CAVENDISH'

'SMT-6'

'GIANT CAVENDISH'

'GIANT CAVENDISH' 'SMT-6'